US008217039B2

United States Patent
Mathad et al.

(10) Patent No.: US 8,217,039 B2
(45) Date of Patent: Jul. 10, 2012

(54) APREPITANT POLYMORPH MIXTURES (75) Inventors: Vijayavitthal Thippannachar Mathad, Hyderabad (IN); Pravinchandra Jayantilal Vankawala, Hyderabad (IN); Raviram Chandrasekhar Elati, Hyderabad (IN); Prabhakar Macharla, Mahaboob Nagar (IN); Srinivas Gangula, Hyderabad (IN); Naveen Kumar Kolla, Hyderabad (IN); Ravi Kumar Komareddy, Hyderabad (IN); Surya Narayana Devarkonda, Hyderabad (IN); Subbareddy Peddireddy, Hyderabad (IN)

(73) Assignees: Dr. Reddy's Laboratories Ltd., Andhra Pradesh, IN (US); Dr. Reddy's Laboratories, Inc., Bridgewater, NJ (US)

( * ) Notice: Subject to any disclaimer, the term of this patent is extended or adjusted under 35 U.S.C. 154(b) by 884 days.

(21) Appl. No.: 12/294,986

(22) PCT Filed: Mar. 29, 2007

(86) PCT No.: PCT/US2007/065474
§ 371 (c)(1),
(2), (4) Date: Sep. 29, 2008

(87) PCT Pub. No.: WO2007/112457
PCT Pub. Date: Oct. 4, 2007

(65) Prior Publication Data
US 2010/0298327 A1 Nov. 25, 2010

Related U.S. Application Data (60) Provisional application No. 60/787,017, filed on Mar. 29, 2006, provisional application No. 60/746,381, filed on May 4, 2006.

(51) Int. Cl.
*A61K 31/53* (2006.01)
*C07D 417/06* (2006.01)
(52) U.S. Cl. ........................................ 514/241; 544/132
(58) Field of Classification Search .................. 514/241; 544/132
See application file for complete search history.

(56) References Cited

U.S. PATENT DOCUMENTS

| | | | |
|---|---|---|---|
| 5,719,147 A | 2/1998 | Dorn et al. | |
| 6,096,742 A * | 8/2000 | Crocker et al. | 514/241 |
| 6,583,142 B2 | 6/2003 | Crocker et al. | |
| 2009/0192161 A1 | 7/2009 | Sawant et al. | |

OTHER PUBLICATIONS

R. Helmy et al., "Characterization and Quantitation of Aprepitant Drug Substance Polymorphs by Attenuated Total Reflectance Fourier Transform Infrared Spectroscopy," Analytical Chemistry, vol. 75, No. 3, pp. 605-611, 2003.

* cited by examiner

*Primary Examiner* — Kamal Saeed
*Assistant Examiner* — Janet L Coppins
(74) *Attorney, Agent, or Firm* — Gilman Pergament LLP (57) ABSTRACT

Intimate mixtures of aprepitant crystalline Form I and crystalline Form II, having specific weight ratios of the forms.

25 Claims, 10 Drawing Sheets

APREPITANT POLYMORPH MIXTURES

INTRODUCTION TO THE INVENTION

The present invention relates to intimate mixtures of polymorphic forms of aprepitant, processes for their preparation, compositions containing them and their methods of use. More specifically the present invention provides intimate mixtures of crystalline polymorphic Form I and Form II of aprepitant, processes for their preparation, compositions containing them, and their methods of use.

Aprepitant is a tachykinin receptor antagonist, has a chemical name 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one, and is structurally represented by Formula I.

Formula I

Aprepitant is useful in the treatment of emesis concomitant with cancer chemotherapy and is manufactured and commercially sold in the market by Merck and Co. under the brand name EMEND™ as capsules. Each capsule of EMEND contains either 80 mg or 125 mg of aprepitant.

U.S. Pat. No. 5,719,147 discloses the preparation of aprepitant and its pharmaceutically acceptable salts, their pharmaceutical compositions and their methods of use.

U.S. Pat. Nos. 6,096,742 and 6,583,142 disclose crystalline Form I and Form II of aprepitant, process for making these forms, pharmaceutical compositions comprising them and their method of use. These patents specifically claim aprepitant Form I substantially free from Form II, and Form II substantially free from Form I of aprepitant.

The process for the preparation of crystalline Form I of aprepitant involves crystallizing aprepitant from ethanol, 2-propanol, acetonitrile and isopropyl acetate. Alternatively Form I is prepared by heating a sample of aprepitant Form II to a temperature range of 215 to 230° C. and cooling to ambient conditions. Further Form I of aprepitant is prepared on a larger scale by suspending aprepitant in a solution of methanol/water in the ratio of 2:1 (v/v), adding seed crystals of Form I and stirring the resultant mixture at about 0-50° C. for a period sufficient to result in the formation of Form I.

The process for the preparation of crystalline Form II of aprepitant is disclosed in Example 75 of U.S. Pat. No. 5,719,147.

Crystalline Form I of aprepitant is reported to have superior properties over other forms of aprepitant, i.e., Form II, in that this form demonstrates superior thermodynamic stability and is non-hygroscopic when compared with other crystalline forms of aprepitant. Further, crystalline Form I of aprepitant has been shown to have a lower solubility (0.9±0.1 mg/ml) when compared with Form II (1.3±0.2 mg/ml) in a 2:1 v/v methanol/water mixture at 0° C. The numeric ratio of these solubilities (1.4) was said to indicate a higher stability of Form I over Form II.

There is a continuing interest in different polymorphic forms of pharmaceutically active compounds. Different morphological forms of the same compound may exhibit significantly different properties such as for example enhanced thermodynamic stability or improved dissolution characteristics among other properties. The discovery of such novel forms and processes to make these forms are of interest to the pharmaceutical formulation scientist as these improved properties could help in developing pharmaceutical dosage forms with improved stability or handling characteristics. It is thus imperative that the pharmaceutical scientist be assured of a single polymorphic form substantially free from other polymorphic forms or that a mixture of different polymorphic forms in specified ratios are used in the preparation of a pharmaceutical formulation.

There is no way to predict the physicochemical properties of different polymorphic forms or whether a given compound could exist in different polymorphic forms. None of the patents mentioned above describe a mixture of different crystalline forms of aprepitant or processes to make such polymorphic forms, which can be utilized in the development and manufacture of pharmaceutical formulations.

Mixture of polymorphic forms can provide a viable alternative to the pharmaceutical formulation scientist in the development of a formulation of aprepitant with improved properties.

Nevertheless, mixture of polymorphic forms of aprepitant and processes for their preparation are desirable.

SUMMARY OF THE INVENTION

The present invention provides an intimate mixture of aprepitant polymorphs Form I and Form II, and processes for the preparation.

In one aspect, the present invention provides an intimate mixture of aprepitant polymorphs Form I and Form II in a ratio of either form to the other as desired, characterized by the X-ray powder diffraction (XRPD) pattern.

In another aspect, the present invention provides a process for the preparation of an intimate mixture of aprepitant polymorphic Form I to Form II in a ratio of either form to the other as desired on a weight basis.

In an embodiment, a process for the preparation of an intimate mixture of aprepitant polymorphic Form I to Form II, in a ratio of either form to the other as desired, comprises:
a) providing a solution comprising aprepitant and a suitable solvent;
b) removing solvent from the solution; and
c) optionally, drying a formed solid.

Another embodiment of the present invention provides a process for the preparation of an intimate mixture of aprepitant polymorphic Form I to Form II in a desired ratio of either form to the other, comprising:
a) providing a solution comprising aprepitant and a suitable solvent;
b) combining an anti-solvent with the solution of a); and
c) optionally, drying a solid formed in b).

Yet another aspect of the present invention provides a pharmaceutical composition containing intimate mixtures of aprepitant polymorphs Form I and Form II in a weight to weight ratio as described above, prepared by the processes of the present invention, together with at least one pharmaceutically acceptable excipient to obtain a pharmaceutical composition.

An embodiment of the invention provides an intimate mixture of aprepitant crystalline Form I and crystalline Form II.

Another embodiment of the invention provides a process for preparing an intimate mixture of aprepitant crystalline Form I and crystalline Form II, comprising:
a) providing a solution comprising aprepitant and a suitable solvent;
b) removing solvent from the solution; and
c) optionally, drying a formed solid.

A further embodiment of the invention provides a process for preparing an intimate mixture of aprepitant crystalline Form I and crystalline Form II, comprising:
a) providing a solution comprising aprepitant and a suitable solvent;
b) combining an anti-solvent with the solution; and
c) optionally, drying a solid formed in b).

An additional embodiment of the invention provides a process for preparing an intimate mixture of aprepitant crystalline Form I and crystalline Form II, comprising:
a) providing a solution comprising aprepitant and acetone;
b) combining water with a solution;
c) maintaining a combination at temperatures lower than a temperature of combining, for a time sufficient to form a solid having a desired ratio of crystalline forms; and
d) optionally, drying a formed solid.

In another embodiment, the invention provides a pharmaceutical composition comprising an intimate mixture of aprepitant crystalline Form I and Form II, wherein a weight ratio of Form I to Form II is about 5:95 to about 95:5, and at least one pharmaceutical excipient.

DETAILED DESCRIPTION OF THE INVENTION

The present invention relates to an intimate mixture of aprepitant polymorphs Form I and Form II, and processes for their preparation.

In one aspect, the present invention provides an intimate mixture of aprepitant polymorphs Form I and Form II in any desired ratio of either form to the other characterized by their X-ray powder diffraction (XRPD) pattern.

By the term "intimate mixture," it is meant that the mixture of aprepitant polymorphs Form I and Form II in any desired ratio has an evenly dispersed, uniform and stable mixture of the polymorphs and has the same composition of the polymorphs throughout the mixture.

"Any desired ratio" of either form to the other includes variable ratios of Form I to Form II between about 5:95 and 95:5, or between about 10:90 and 90:10, or between about 25:75 and 75:25, by weight, including, but not limited to, about 5% w/w to about 95% w/w, or about 20% w/w to about 80% w/w, or about 70% w/w to about 30% w/w, or about 50% w/w to about 50% w/w, or about 95% w/w to about 5% w/w, or about 75% w/w to about 25% w/w, or about 60% w/w to about 40% w/w.

The term "stable" is used to describe an intimate mixture of aprepitant Form I and Form II that maintains an initial weight ratio of forms during formulation into a pharmaceutical dosage form and thereafter during a commercially useful period of normal storage and use, such as about one year, about 18 months, about two years, or any other desired period. Stability is typically indicated by maintenance of the weight ratio of forms during stability testing, involving storage under standard conditions, such as those described in Test 1150 "Pharmaceutical Stability," *United States Pharmacopeia* 29, United States Pharmacopeial Convention, Inc., Rockville, Md., 2005, at pages 2994-2995. Stability testing procedures are well known in the pharmaceutical industry.

The amounts of Form I and Form II of aprepitant are expressed throughout the application as weight ratios or as weight percent. Weight percent is intended to mean: [(either Form I or Form II weight)÷(Form I+Form II weight)]×100.

The above mentioned intimate mixtures of crystalline forms of aprepitant are characterized by their X-ray powder diffraction ("XRPD") patterns. All XRPD information herein was generated on a Bruker AXS, D8 Advance Powder X-ray Diffractometer with a Cu K alpha-1 radiation source.

The XRPD patterns of the intimate mixtures of forms have the characteristic peaks of both crystalline Form I and Form II of aprepitant. Depending on the weight ratios of the forms, the intensities of characteristic peaks will vary.

The crystalline Form I of aprepitant is characterized by its XRPD pattern having significant peaks at about 15.3, 12.0, 17.6, 20.6, 24.7, and 29.2, ±0.2 degrees 2θ. It is also characterized by additional XRPD peaks at about 16.6, 17.0, and 20.0, ±0.2 degrees 2θ.

The crystalline Form II of aprepitant is characterized by its XRPD pattern having significant peaks at about 21.2, 12.7, 16.3, 16.9, 17.2, 20.3, 18.2, 24.9, and 24.0, ±0.2 degrees 2θ. It is also characterized by additional XRPD peaks at about 12.2, 14.5, and 26.7, ±0.2 degrees 2θ.

Characteristic XRPD patterns for intimate mixtures having ratios of Form I to Form II about 5% w/w to about 95% w/w, about 20% w/w to about 80% w/w, about 70% w/w to about 30% w/w, about 95% w/w to about 5% w/w, about 75% w/w to about 25% w/w, about 60% w/w to about 40% w/w, about 50% w/w to about 50% w/w, about 25% w/w to about 75% w/w, and about 80% w/w to about 20% w/w are given in FIGS. 1, 2, 3, 4, 5, 6, 7, 8 and 9, respectively.

In a specific embodiment, the present invention provides an intimate mixture having a ratio of Form I to Form II about 50% w/w to about 50% w/w.

When there is a simple physical mixture of particles of polymorphic forms with varying stability, there is a general expectation of the mixture converting to the more stable form with the passage of time, or when exposed to extreme environmental conditions.

A 50:50 by weight intimate mixture of aprepitant polymorphic Forms I and II prepared according to the present invention does not convert to the more stable Form I upon subjection to stress conditions. It has been found that the composition of the mixture is maintained even after milling, micronization, or drying at temperatures of about 90° C. for prolonged periods of time.

In another aspect, the present invention provides a process for the preparation of an intimate mixture of aprepitant polymorphic Form I to Form II in a ratio of either form to the other as desired on a weight to weight basis.

In an embodiment, the process for the preparation of an intimate mixture of aprepitant polymorphic Form I to Form II in a ratio of either form to the other as desired comprises:

a) providing a solution comprising aprepitant and a suitable solvent;
b) removing solvent from the solution; and
c) optionally, drying a formed solid.

Step a) involves providing a solution comprising aprepitant and a suitable solvent.

The solution of aprepitant may be obtained by dissolving aprepitant in a suitable solvent, or such a solution may be obtained directly from a reaction in which aprepitant is formed.

When the solution is prepared by dissolving aprepitant in a suitable solvent, any form of aprepitant such as a crystalline or amorphous form, including any salts, solvates and hydrates may be utilized for preparing the solution.

Organic solvents that can be used in the dissolution of aprepitant include, but are not limited to: alcohols such as methanol, ethanol, isopropyl alcohol, isobutyl alcohol, tertiary butyl alcohol and the like; halogenated hydrocarbons such as dichloromethane ("DCM"), ethylene dichloride, chloroform and the like; ketones such as acetone, methyl isobutyl ketone and the like; nitriles such as acetonitrile, propionitrile and the like; ethers such as dimethyl ether, diethyl ether, diisopropyl ether, tetrahydrofuran ("THF"), methyl tertiary-butyl ether and the like; esters such as ethyl acetate, n-propyl acetate, isopropyl acetate, n-butyl acetate, isobutyl acetate and the like; and aprotic polar solvents such as dimethyl sulfoxide ("DMSO"), N,N-dimethylformamide, N,N-dimethylacetamide and the like. Any solvent or mixture of solvents or their combination with water or any of the solvents from the classes mentioned above is acceptable for the preparation of the solution of aprepitant as long as it has a good enough solubility for any polymorphic form of aprepitant and is not detrimental chemically or physically to aprepitant.

The dissolution temperatures can range from about 20 to 120° C. depending on the solvent used for dissolution. Any other temperature is also acceptable as long as a clear solution of aprepitant is provided.

The quantity of solvent used for dissolution depends on the solvent and the dissolution temperature adopted. The concentration of aprepitant in the solution may generally range from about 0.1 to about 10 g/ml in the solvent.

Optionally, the solution obtained above can be filtered to remove the undissolved particles followed by further processing.

The undissolved particles can be removed suitably by filtration, centrifugation, decantation, and other techniques. The solution can be filtered by passing through paper, glass fiber, or other membrane material, or a bed of a clarifying agent such as celite. Depending upon the equipment used and the concentration and temperature of the solution, the filtration apparatus may need to be preheated to avoid premature crystallization.

Step b) involves removing solvent from the solution.

Removal of the solvent may be carried out suitably using techniques such as evaporation, atmospheric distillation, or distillation under vacuum.

Any temperature ranging from about 20° C. to about 120° C. can be used for distillation of the solvent. The temperature chosen for distillation determines the percentages of the polymorphic Forms I and II in the product.

If the distillation is carried out under vacuum, a vacuum of the range of below about 100 mm Hg to below about 600 mm Hg can be applied.

As mentioned in the prior art, Form I is thermodynamically more stable than polymorphic Form II. Higher temperatures during distillation lead to a higher percentage of Form I in the mixture, and lower temperatures give higher percentages of Form II.

Also the duration of distillation plays an important role. Distillation for longer periods leads to a higher percentage of the stable Form I. This may be attributed to the conversion of the unstable Form I to a more stable Form I during the period when temperatures are elevated.

When the distillation is carried out in the absence of vacuum, the use of lower temperatures leads to longer elevated temperature maintenance time, leading to higher percentages of Form I in the product.

By suitably adjusting the temperature and vacuum conditions, the desired ratio of Form I and Form II can be obtained in the intimate mixture.

Removal of solvent from the solution obtained in step a) using a Buchi Rotavapor at a temperature of about 30 to about 35° C., and a pressure of about 300 to about 600 mm Hg affords an intimate mixture of aprepitant polymorphic Form I to Form II in a ratio of about 5% w/w to about 95% w/w.

Removal of solvent from the solution obtained in step a) using a Buchi Rotavapor at a temperature of about 45° C. to about 50° C. and a pressure of about 300 to about 600 mm Hg affords an intimate mixture of aprepitant polymorphic Form I to Form II in a ratio of about 20% w/w to about 80% w/w.

Removal of solvent from the solution obtained in step a) using a Buchi Rotavapor at a temperature of about 60° C. to about 65° C. and a pressure of about 300 to about 600 mm Hg affords an intimate mixture of aprepitant polymorphic Form I to Form II in a ratio of about 75% w/w to about 25% w/w.

Removal of solvent from the solution obtained in step a) using a conventional distillation without the use of vacuum at 30-35° C. affords an intimate mixture of aprepitant polymorphic Form I to Form II in a ratio of about 95% w/w to about 5% w/w.

Removal of solvent from the solution obtained in step a) using a conventional distillation without the use of vacuum at 45-50° C. affords an intimate mixture of aprepitant polymorphic Form I to Form II in a ratio of about 75% w/w to about 25% w/w.

Other ratios of the crystalline Forms I and II ranging from about 5% to 95% w/w of Form I in Form II, or Form II in Form I, can be prepared by using either of the techniques of distillation and varying the temperatures accordingly.

The intimate mixture of forms obtained from step b) can be collected from the equipment using techniques such as by scraping, or by shaking the container, or using a technique specific to the particular apparatus employed.

Step c) involves optionally drying a solid obtained from step b).

Drying can be carried out with or without applying vacuum at temperatures such as about 35° C. to about 70° C. The drying can be carried out for any desired time period that achieves the desired product purity, such as times about 1 to 20 hours, or longer. Drying may also be carried out for shorter or longer periods of time depending on the product specifications.

In yet another aspect, the present invention provides an alternative process for the preparation of an intimate mixture of aprepitant polymorphic Form I to Form II in a desired ratio of either form to the other, comprising:

a) providing a solution comprising aprepitant and a suitable solvent;
b) combining an anti-solvent with the solution of a); and
c) optionally, drying a solid formed in b).

Step a) involves providing a solution of aprepitant in a suitable solvent.

The solution of aprepitant may be obtained by dissolving aprepitant in a suitable solvent, or such a solution may be obtained directly from a reaction in which aprepitant is formed.

When the solution is prepared by dissolving aprepitant in a suitable solvent, any form of aprepitant such as a crystalline or amorphous form, including any salts, solvates and hydrates may be utilized for preparing the solution.

Organic solvents that can be used in the dissolution of aprepitant include, but are not limited to: alcohols such as methanol, ethanol, isopropyl alcohol, isobutyl alcohol, tertiary-butyl alcohol and the like; halogenated hydrocarbons such as dichloromethane, ethylene dichloride, chloroform and the like; ketones such as acetone, methyl isobutyl ketone and the like; nitriles such as acetonitrile, propionitrile and the like; ethers such as dimethyl ether, diethyl ether, diisopropyl ether, tetrahydrofuran, methyl tertiary-butyl ether and the like; esters such as ethyl acetate, n-propyl acetate, isopropyl acetate, n-butyl acetate, isobutyl acetate and the like; and aprotic polar solvents such as dimethyl sulfoxide, N,N-dimethylformamide, N,N-dimethylacetamide and the like. Any solvent or mixture of solvents or their combination with water or any of the solvents from the classes mentioned above is acceptable for the preparation of the solution of aprepitant as long as it has a good enough solubility for any polymorphic form of aprepitant and is not detrimental chemically or physically to aprepitant.

The dissolution temperatures can range from about 20 to 120° C. depending on the solvent used for dissolution. Any other temperature is also acceptable as long as a clear solution of aprepitant is provided.

The quantity of solvent used for dissolution depends on the solvent and the dissolution temperature adopted. The concentration of aprepitant in the solution may generally range from about 0.1 to about 10 g/ml in the solvent. Higher concentrations, up to the solubility limit, generally provide a greater product recovery and a resulting higher process efficiency.

Optionally, the solution obtained above can be filtered to remove any undissolved particles followed by further processing.

The undissolved particles can be removed suitably by filtration, centrifugation, and other techniques. The solution can be filtered by passing through paper, glass fiber, or other membrane material, or a bed of a clarifying agent such as celite. Depending upon the equipment used and the concentration and temperature of the solution, the filtration apparatus may need to be preheated to avoid premature crystallization.

Step b) involves combining an anti-solvent with the solution of step a).

Crystallization of the desired ratio of mixture of forms may be initiated by adding an anti-solvent to the solution of step a).

Suitable solvents which can be used as anti-solvents include, but are not limited to: water; $C_5$ to $C_{12}$ saturated hydrocarbons such as hexane and heptane and the like; ethers such as methyl t-butyl ether, di-isopropyl ether and methyl ethyl ether and the like; and mixtures thereof.

The ratios of the polymorphic forms in the final product vary depending on the crystallization temperature, crystallization time, and the duration of addition of the anti-solvent. The combination contains from about 5% to about 95%, or about 10% to about 90%, by weight of Form II, the remainder being Form I, or vice versa.

Higher temperatures during crystallization lead to higher percentages of Form I, because of its higher thermodynamic stability, and lower temperatures give higher percentages of Form II.

The mass may be maintained further at temperatures lower than the temperatures of anti-solvent addition, such as for example below about 25° C., or below about 10° C., or below about 5° C., for a period of time as required for a more complete isolation of the product. The exact cooling temperature and time required for complete crystallization can be readily determined by a person skilled in the art and will also depend on parameters such as concentration and temperature of the solution or slurry.

Extended maintenance times also lead to a higher percentage of Form I, due to the conversion of the less stable Form I to the more stable Form II during the extended maintenance period. In a similar manner, duration of addition of the anti-solvent also plays an important role in determining the percentages of Form I and Form II in the resultant mixture; longer addition times leading to a higher percentage of polymorphic Form I of aprepitant. Therefore, simple experimentation can be used to determine the particular ratios of forms that will be obtained from varying the maintenance times, when the other processing conditions are kept constant.

One skilled in the art will appreciate that the present invention is not limited by the order of the additions in combining with an anti-solvent. For example, a solution may be added to an anti-solvent or vice versa, though convenience considerations may prefer one over the other. Crystallization of a compound is often better when a solution is added to the anti-solvent, but operationally it is often more convenient to add the anti-solvent to the solution. When adding an anti-solvent to a solution, the order of addition is of minimal relevance. The term "combining" encompasses both orders of addition.

The method by which a solid material is isolated from the mixture, with or without cooling below the operating temperature, can be any of techniques such as filtration by gravity or by suction, decantation, centrifugation, and the like. The crystals so isolated will carry a small proportion of occluded mother liquor. If desired the crystals can be washed with a solvent. The solvent used for washing the crystals may be the one used in step a) for dissolution, or the material that was used as the anti-solvent, or some other solvent.

Optionally small amounts of seed crystals of the desired ratio of Form I to Form II in the product may be added to the solution before, during, or after the addition of the anti-solvent. Small amounts include about 1 to 20 weight percent, or about 5 weight percent.

Seeding allows for manipulating the ratio of Forms I and II relative to each other. The seeding also allows for crystallization in a more consistent ratio.

Step c) involves optionally drying a solid formed in b).

A wet cake obtained from step b) may optionally be further dried. Drying can be suitably carried out in a tray dryer, vacuum oven, air oven, or using a fluidized bed drier, spin flash dryer, flash dryer and the like. The drying can be carried out at temperatures of about 35° C. to about 70° C. The drying can be carried out for any time periods needed for achieving a desired product purity, such as times about 1 to 20 hours, or longer.

The intimate mixtures of aprepitant polymorphic Forms I and II of the present invention are stable and well suited for use in pharmaceutical formulations.

The intimate mixtures of aprepitant polymorphs Form I and Form II prepared according to this embodiment typically have mean particle sizes greater than about 2 µm or 15 µm. If smaller particles and/or specific particle size distributions are required for subsequent processing, such as formulation into pharmaceutical dosage forms, appropriate size reduction procedures such as milling, grinding, etc. can be used. In addition, classification procedures can be used to separate certain particle size fractions.

The $D_{10}$, $D_{50}$ and $D_{90}$ values are useful ways for indicating a particle size distribution. $D_{90}$ refers to the value for the particle size for which at least 90 volume percent of the particles have a size smaller than the value. Likewise $D_{50}$ and $D_{10}$ refer to the values for the particle size for which 50 volume percent, and 10 volume percent, of the particles have a size smaller than the value. Methods for determining $D_{10}$, $D_{50}$ and $D_{90}$ include laser light scattering, such as using equipment from Malvern Instruments Ltd. (of Malvern, Worcestershire, United Kingdom).

Aprepitant intimate mixtures of forms prepared according to the invention have: $D_{10}$ less than about 10 µm, or less than about 20 µm; $D_{50}$ less than about 50 µm, or less than about 40 µm; and $D_{90}$ less than about 400 µm, or less than about 300 µm. There is no specific lower limit for any of the D values.

In a still another aspect, the invention provides a pharmaceutical composition of an intimate mixture of aprepitant polymorphs Form I and Form II in a weight to weight ratio as described above, prepared by the processes of the present invention and combining the mixture with at least one pharmaceutically acceptable excipient to obtain a pharmaceutical composition.

The intimate mixtures of crystalline Form I and Form II of aprepitant of the present invention are ideally suited for incorporation into pharmaceutical compositions. Thus, according to this embodiment of the invention a pharmaceutical composition contains at least one pharmaceutically acceptable excipient in addition to the aprepitant. The different pharmaceutically acceptable excipients which can be added to the pharmaceutical composition include but are not limited to diluents, binders, disintegrants, wetting agents, glidants, colorants, emulsifiers, coating agents, thickening agents, antioxidants, preservatives, buffering agents, crystallization preventing agents and the like, depending upon the kind of pharmaceutical composition envisaged.

The mixtures of polymorphic forms of the invention can be incorporated into pharmaceutical compositions such as for example tablets, mini tablets, capsules, powders, granulates, aggregates, suppositories, sachets, troches, lozenges and the like. Controlled release formulations comprising the combinations of the invention are also possible. Liquid formulations in which the combinations are utilized are also envisaged such as for example syrups, suspensions, dry powders for suspension, and the like.

The present invention provides a process suitable for use on an industrial scale for preparation of formulations/compositions of aprepitant. Aprepitant may be crystallized as an intimate mixture of polymorphs in such a way that the ratio between the polymorphs is consistent. As used herein, a "consistent ratio" (or consistent intimate mixture) refers to a ratio of Form I to Form II (wt/wt) that varies within a range of less than about ±10% (wt/wt) between lots, as measured by XRPD.

The pharmaceutical compositions comprising the mixtures of crystalline Form I and Form II of the invention are useful in the treatment of emesis and a variety of other maladies in mammals, specifically human beings. These and other maladies are described in U.S. Pat. No. 6,583,142 and are all included herein by reference.

Certain specific aspects and embodiments of the present invention will be explained in more detail with reference to the following examples, which are provided by way of illustration only and should not be construed as limiting the scope of the invention in any manner.

Example 1

Preparation of 5:95 Ratio of a Combination of Aprepitant Polymorphic Forms I and II Using a Distillation Process 5 g of aprepitant, 250 ml of dichloromethane, 5 ml of methanol and 0.5 ml of 50% aqueous ammonia were charged into a clean and dry round bottom flask followed by stirring for 10 minutes. The solution was distilled completely at about 32° C. in a Buchi Rotavapor under a vacuum of 600 mm Hg. The wet solid obtained was dried at 45° C. for 12 hours to afford 5 g of the title compound in the desired intimate mixture of aprepitant polymorphic Form I to Form II in a weight to weight ratio of about 5% w/w to about 95% w/w.

Calculation of Form II content:

% of Form $II=[(S2/S1)\div K=(S2/S1)]\times 100$

S1=Area of peak corresponding to Form I
S2=Area of peak corresponding to Form II
K=Response factor between Form II and Form I=0.32 for aprepitant Form I and Form II mixture.

Form $II=[(7.867/0.552)/0.32+(7.867/0.552)]\times 100=97.8\%$

Example 2

Preparation of 20:80 Ratio of a Combination of Aprepitant Polymorphic Forms I and II Using a Distillation Process 5 g of aprepitant, 250 ml of dichloromethane, 5 ml of methanol and 0.5 ml of 50% aqueous ammonia were charged into a clean and dry round bottom flask followed by stirring for 10 minutes. The solution was distilled completely at 48° C. in a Buchi Rotavapor under a vacuum of 600 mm Hg. The wet solid obtained was dried at 45° C. for 12 hours to afford 5 g of the desired intimate mixture of aprepitant polymorphs Form I to Form II in a weight to weight ratio of about 20% w/w to about 80% w/w.

% of Form $II=[(S2/S1)\div K=(S2/S1)]\times 100$

Form $II=[(3.615/2.9)/0.32+(3.615/2.9)]\times 100=79.5\%$.

Example 3

Preparation of a 75:25 Ratio of a Combination of Aprepitant Polymorphic Forms I and II Using a Distillation Process 5 g of aprepitant, 250 ml of dichloromethane, 5 ml of methanol and 0.5 ml of 50% aqueous ammonia were charged into a clean and dry round bottom flask followed by stirring for 10 minutes. The solution was distilled completely at about 64° C. in a Buchi Rotavapor at atmospheric pressure. The solid obtained was dried aerially at 45° C. for 12 hours to afford 5 g of the desired intimate mixture of aprepitant polymorphic Form I to II in a weight to weight ratio of about 75% w/w to about 25% w/w.

% of Form $II=[(S2/S1)\div K+(S2/S1)]\times 100$

Form $II=[(0.849/6.739)/0.32+(0.849/6.739)]\times 100=28.24\%$.

Example 4

Preparation of 95:5 Ratio of a Combination of Aprepitant Polymorphic Forms I and II Using a Distillation Process

5 g of aprepitant, 250 ml of dichloromethane, 5 ml of methanol and 0.5 ml of 50% aqueous ammonia were charged into a clean and dry round bottom flask followed by stirring for 10 minutes. The solution was distilled completely at 35° C. in a 4 neck round bottom flask under a vacuum of 600 mm Hg. The solid obtained was dried at 45° C. for 10 hours to afford 5 g of the desired intimate mixture of aprepitant polymorphic Form I to II in a weight to weight ratio of about 95% w/w to about 5% w/w.

Example 5

Preparation of 75:25 Ratio of a Combination of Aprepitant Polymorphic Forms I and II Using a Distillation Process

5 g of aprepitant, 250 ml of dichloromethane, 5 ml of methanol and 0.5 ml of 50% aqueous ammonia were charged into a clean and dry round bottom flask followed by stirring for 10 minutes. The solution was distilled completely at about 49° C. in a 4 neck round bottom flask under a vacuum of 600 mm Hg. The wet solid obtained was dried at 45° C. for 10 hours to afford 5 g of the desired intimate mixture of aprepitant polymorphic Form I to II in a weight to weight ratio of about 75% w/w to about 25% w/w.

Example 6

Preparation of a 60:40 Ratio of a Combination of Aprepitant Polymorphs I and II Using a Distillation Process

5 g of aprepitant, 250 ml of dichloromethane (DCM), 5 ml of methanol and 0.5 ml of 50% aqueous ammonia were charged into a clean and dry round bottom flask followed by stirring for 15 minutes. The solution was distilled completely at about 64° C. in a 4 neck round bottom flask at atmospheric pressure. The wet solid obtained was dried at 45° C. for 10 hours to afford 5 g of the desired intimate mixture of aprepitant polymorphic Form I to II in a weight to weight ratio of about 60% w/w to about 40% w/w.

Example 7

Preparation of a 50:50 Ratio of a Combination of Aprepitant Polymorphs Form I and Form II Using Solvent-Antisolvent Technique

0.5 g of aprepitant and 12 ml of methanol were charged into a clean and dry round bottom flask to obtain a suspension. The suspension was heated to 65° C. for clear dissolution, followed by the charging of 0.05 g of a seeding intimate mixture of crystalline Form I and Form II (50:50 w/w) with stirring. The resultant suspension was cooled to 35° C., followed by charging of 0.5 ml of water. The suspension was stirred for 30 minutes followed by filtration of the solid and washing with 6 ml of methanol. The solid obtained was dried for 3 hours under a vacuum of 600 mm Hg to afford 0.4 g of an intimate mixture of aprepitant polymorphs Form I and Form II in a weight ratio of 50:50.

Particle size distribution: $D_{10}$ less than 6.4 µm; $D_{50}$ less than 16.2 µm; and $D_{90}$ less than 34.9 µm.

Example 8

Preparation of a 70:30 Ratio of Aprepitant Polymorphs Form I and Form II by Solvent-Antisolvent Technique

2.0 g of aprepitant and 30 ml of acetone were taken into a round bottom flask and stirring and heated to 56° C. to get clear dissolution. The solution was then cooled to 30° C. and 30 ml of water was added. The mass was maintained at 30° C. for 5 minutes. The separated solid was filtered and the wet solid was dried at 50° C. under a vacuum of 700 mm Hg for 2 hours to get 1.5 g of the title intimate mixture.

Weight ratio of Form I to Form II=68.4:31.6.

Example 9

Preparation of a 25:75 Ratio of Aprepitant Polymorphs Form I and Form II by Solvent-Antisolvent Technique

2.0 g of aprepitant and 30 ml of acetone were taken into a round bottom flask with stirring and heating to 57° C. to get clear dissolution. The solution was then cooled to 2 to 3° C. and 30 ml of water was added. The reaction mass was maintained at 2 to 3° C. for 5 minutes. The separated solid was filtered and the wet solid was dried at 50° C. under a vacuum of 700 mm Hg for 2 hours to get 1.67 g of the title intimate mixture.

Weight ratio of Form I to Form II=24.9:75.1.

Example 10

Preparation of a 10:90 Ratio of Aprepitant Polymorphs Form I and Form II by Solvent-Antisolvent Technique

2.0 g of aprepitant and 20 ml of methanol were taken into a round bottom flask with stirring and heating to 65° C. to get clear dissolution. The solution was then cooled to 30° C. and 10 ml of water was added. The mass was maintained at 30° C. for 5 minutes. The separated solid was filtered and the wet solid was dried at 50° C. under a vacuum of 700 mm Hg for 2 hours to get 1.4 g of the title intimate mixture.

Weight ratio of Form I to Form II=11:89.

Example 11

Preparation of a 80:20 Ratio of Aprepitant Polymorphs Form I and Form II by Solvent-Antisolvent Technique

2.0 g of aprepitant and 5 ml of methanol were taken into a round bottom flask with stirring and heating to 65° C. to get clear dissolution. The solution was then cooled to 2° C. and 5 ml of water was added in two equal lots. The reaction mass was maintained at 2° C. for 5 minutes. The separated solid was filtered and the wet solid was dried at 50° C. under a vacuum of 700 mm Hg for 2 hours to get 0.5 g of the title intimate mixture.
Weight ratio of Form I to Form II=82:18.

Example 12

Preparation of a 50:50 Ratio of Aprepitant Polymorphs Form I and Form II by Solvent-Antisolvent Technique 600 ml of acetone was taken into a reactor and 40 g of aprepitant was added at 29° C., with stirring and heating to 57° C. to get clear dissolution. The solution was then cooled to 3° C. and 600 ml of water was added. The mass was maintained at 0 to 3° C. for 3 hours. The separated solid was filtered and the wet solid was dried at 50° C. under a vacuum of 700 mm Hg for 4 hours to get 36.5 g of the title intimate mixture.
Weight ratio of Form I to Form II=47:53.

Example 13

Preparation of Different Ratios of Aprepitant Polymorphs Form I and Form II by Solvent-Antisolvent Technique 2 g of aprepitant was dissolved in an organic solvent at a suitable temperature, then water was added as an anti-solvent to the solution of aprepitant at 25 to 30° C. The mixture was maintained at 30° C. for 5 minutes, and then filtered. The results of the percentages of Form I and Form II in the corresponding products are tabulated below:

| Solvent Used for Dissolution (Solvent/Quantity) | Quantity of Anti-solvent | Volume Ratio of Solvent:Anti-solvent | Form II, wt. % |
| --- | --- | --- | --- |
| Methanol-DCM (10:1 by volume)/30 ml | 15 ml | 2:1 | 71.5 |
| Acetone/30 ml | 30 ml | 1:1 | 31.6 |
| Methanol/20 ml | 10 ml | 2:1 | 89 |
| DMSO/5 ml | 5 ml | 1:1 | ND |
| THF/5 ml | 5 ml | 1:1 | 26 |

Example 14

Preparation of a Ratio of 70:30 to 30:70 of Aprepitant Form I and Form II Using Acetone as Solvent and Water as Anti-Solvent Aprepitant and acetone were taken into a round bottom flask and stirred and heated to 57° C. to get clear dissolution. The solution was then cooled to 2 to 3° C. and water was added. The mass was maintained at 2 to 3° C. Samples were analyzed at different maintenance times starting at 5 minutes to 8 hours to determine the effect of the duration of maintenance on the ratio of polymorphic Forms I and II in the product. The results are tabulated below:

| Batch Size (g) | Acetone/Water (ml) | Maintenance (Minutes) | Form II, wt. % |
| --- | --- | --- | --- |
| 2 | 30/30 | 5 | 75 |
| 1.25 | 18.75/18.75 | 120 | 60.4 |
| 50 | 750/750 | 180 | 53.4 |
| 1.25 | 18.75/18.75 | 240 | 48.5 |
| 1.25 | 18.75/18.75 | 360 | 30.3 |
| 1.25 | 18.75/18.75 | 480 | 29.1 |

Example 15

Preparation of a 80:20 Ratio of Aprepitant Polymorphs Form I and Form II Using Acetone as Solvent and Water as Anti-Solvent 2.0 g of aprepitant and 30 ml of acetone is taken into a round bottom flask and is stirred and heated to 57° C. to get clear dissolution. The solution is then cooled to 2 to 3° C. and 30 ml of water is added. The mass is maintained at 2 to 3° C. for 15 hours. The separated solid is filtered and the wet solid is dried at 50° C. under a vacuum of 700 mm Hg for 4 hours to get 1.7 g of the title intimate mixture. Weight ratio of Form I to Form II=80:20.

Example 16

Preparation of a 90:10 Ratio of Aprepitant Polymorphs Form I and Form II Using Acetone as Solvent and Water as Anti-Solvent 2.0 g of aprepitant and 30 ml of acetone is taken into a round bottom flask and is stirred and heated to 57° C. to get clear dissolution. The solution is then cooled to 2 to 3° C. and 30 ml of water is added. The mass is maintained at 2 to 3° C. for 24 hours. The separated solid is filtered and the wet solid is dried at 50° C. under a vacuum of 700 mm Hg for 4 hours to get 1.8 g of the title intimate mixture. Weight ratio of Form I to Form II=90:10.

Figure 1:
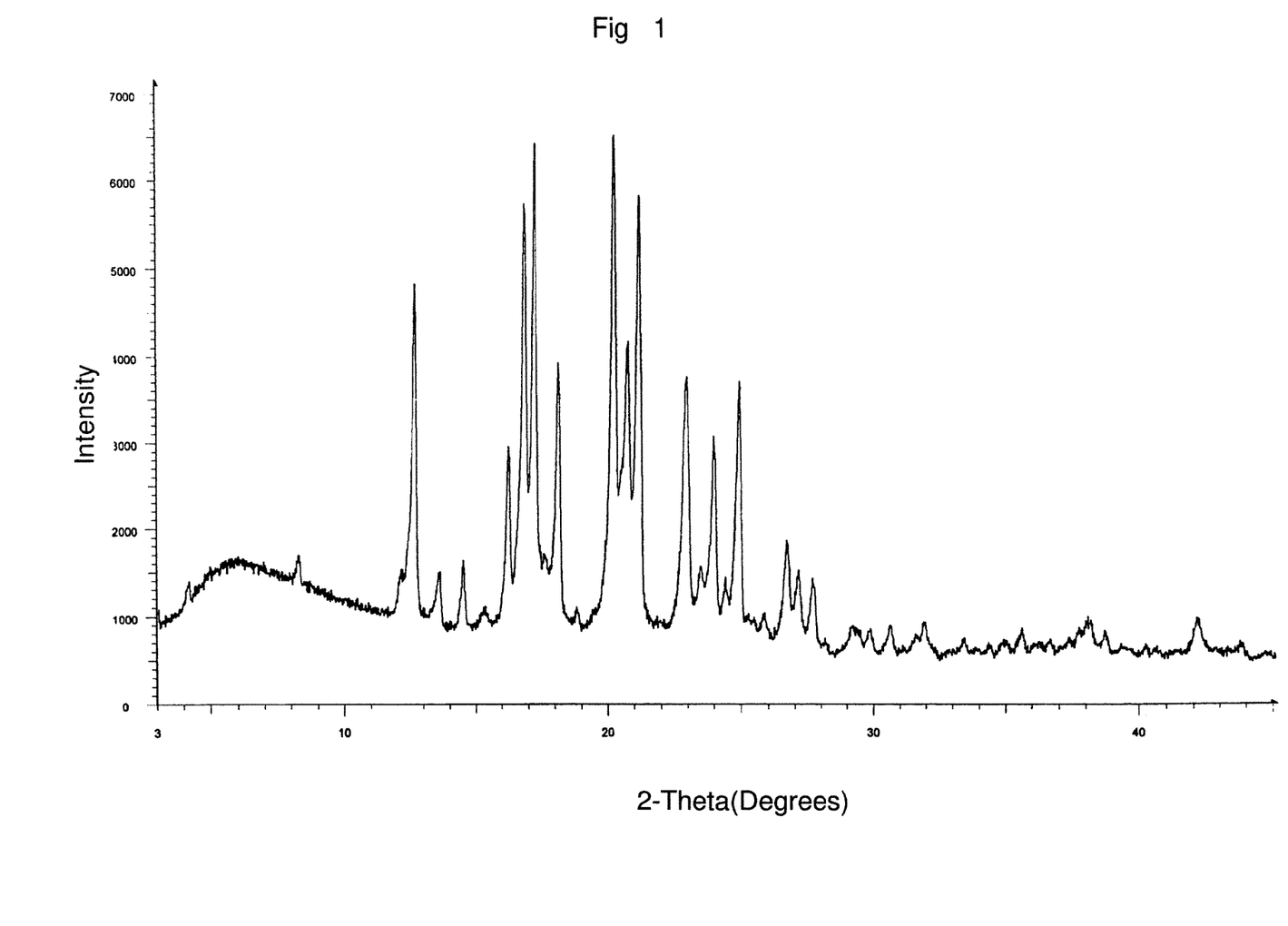
FIG. 1 is an XRPD pattern of an intimate mixture of aprepitant polymorphic Forms I and II in a ratio of about 5:95 w/w, prepared according to Example 1.
Figure 2:
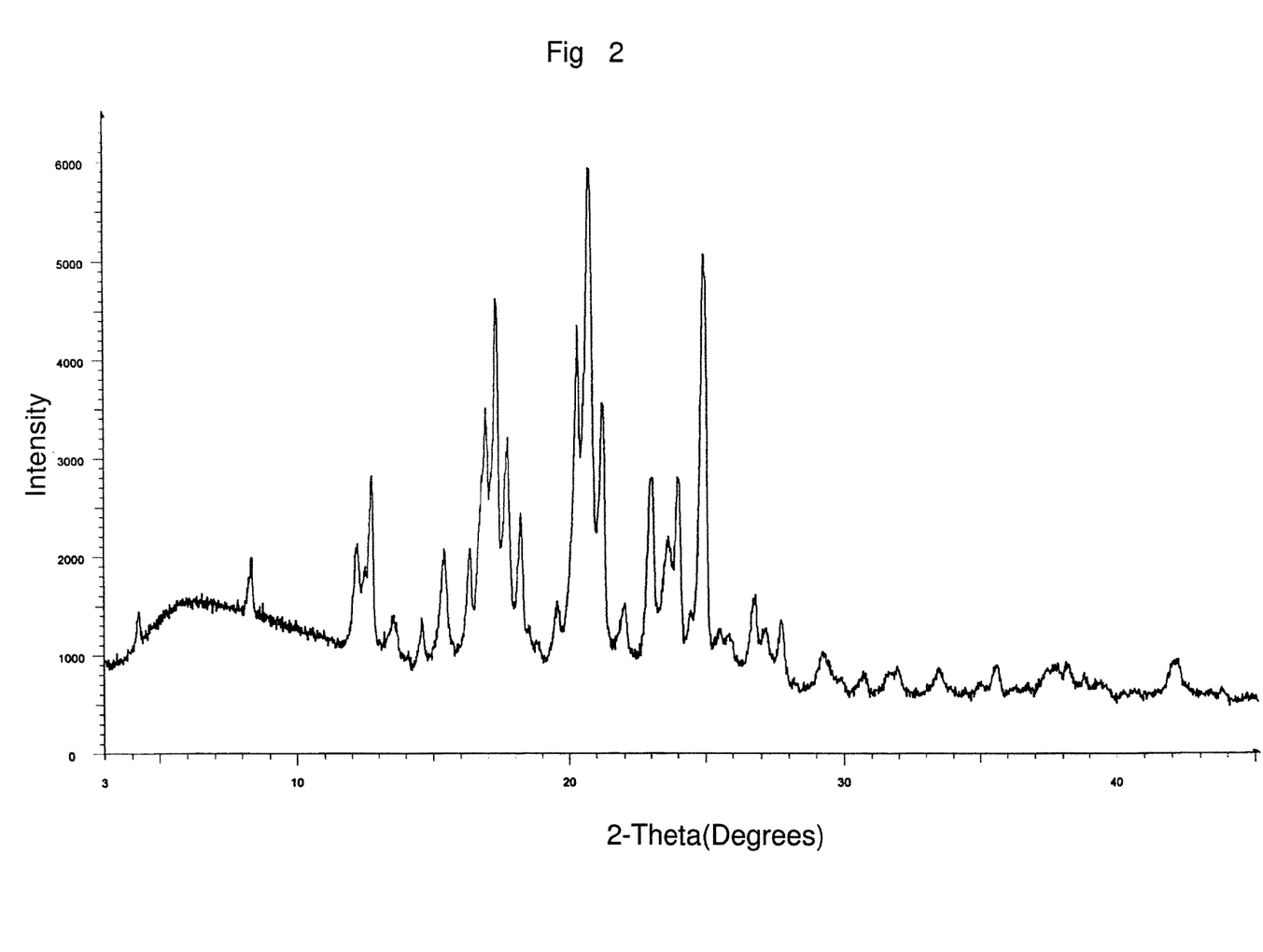
FIG. 2 is an XRPD pattern of an intimate mixture of aprepitant polymorphic Forms I and II in a ratio of about 20:80 w/w, prepared according to Example 2.
Figure 3:
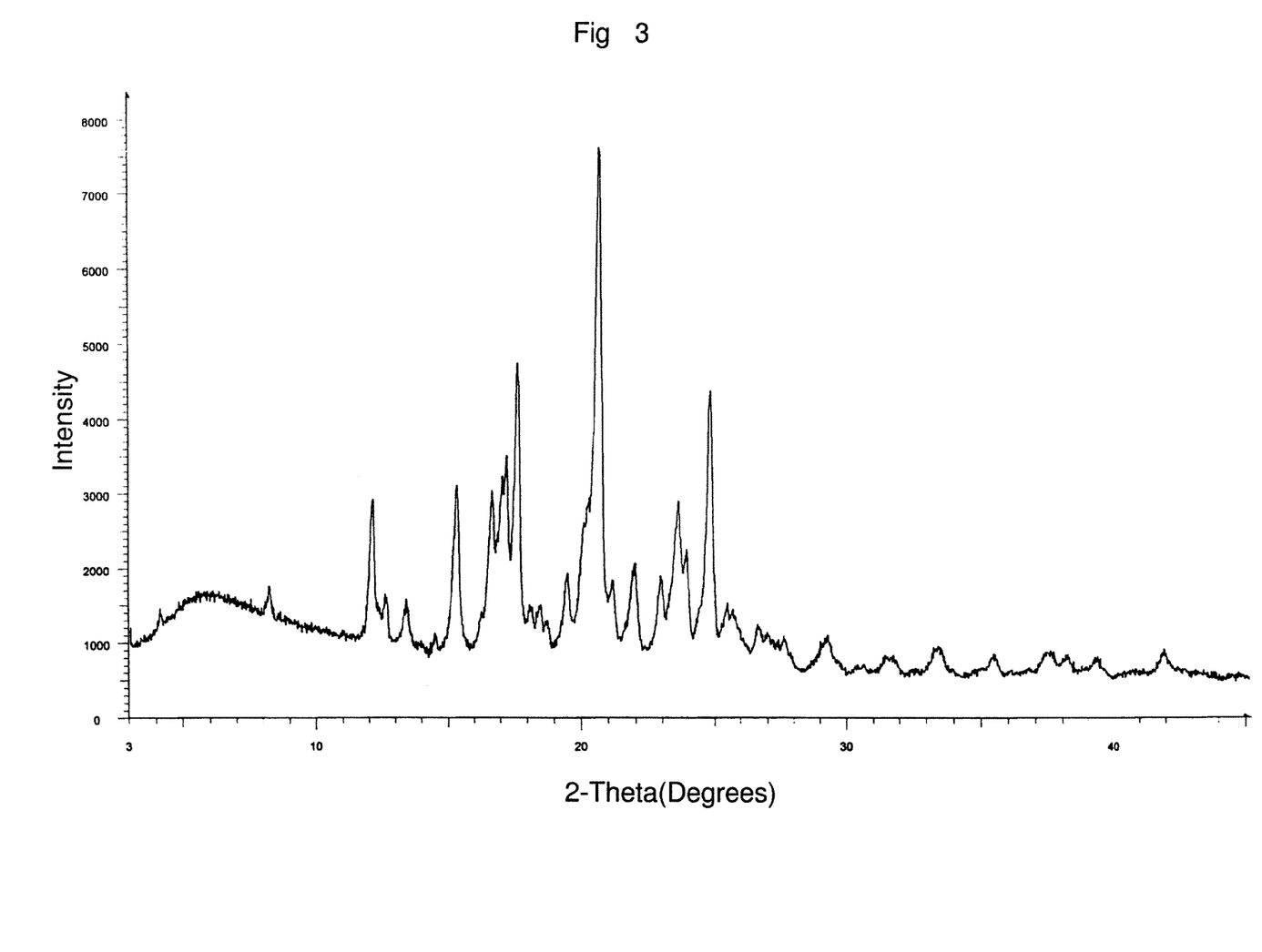
FIG. 3 is an XRPD pattern of an intimate mixture of aprepitant polymorphic Forms I and II in a ratio of about 70:30 w/w, prepared according to Example 3.
Figure 4:
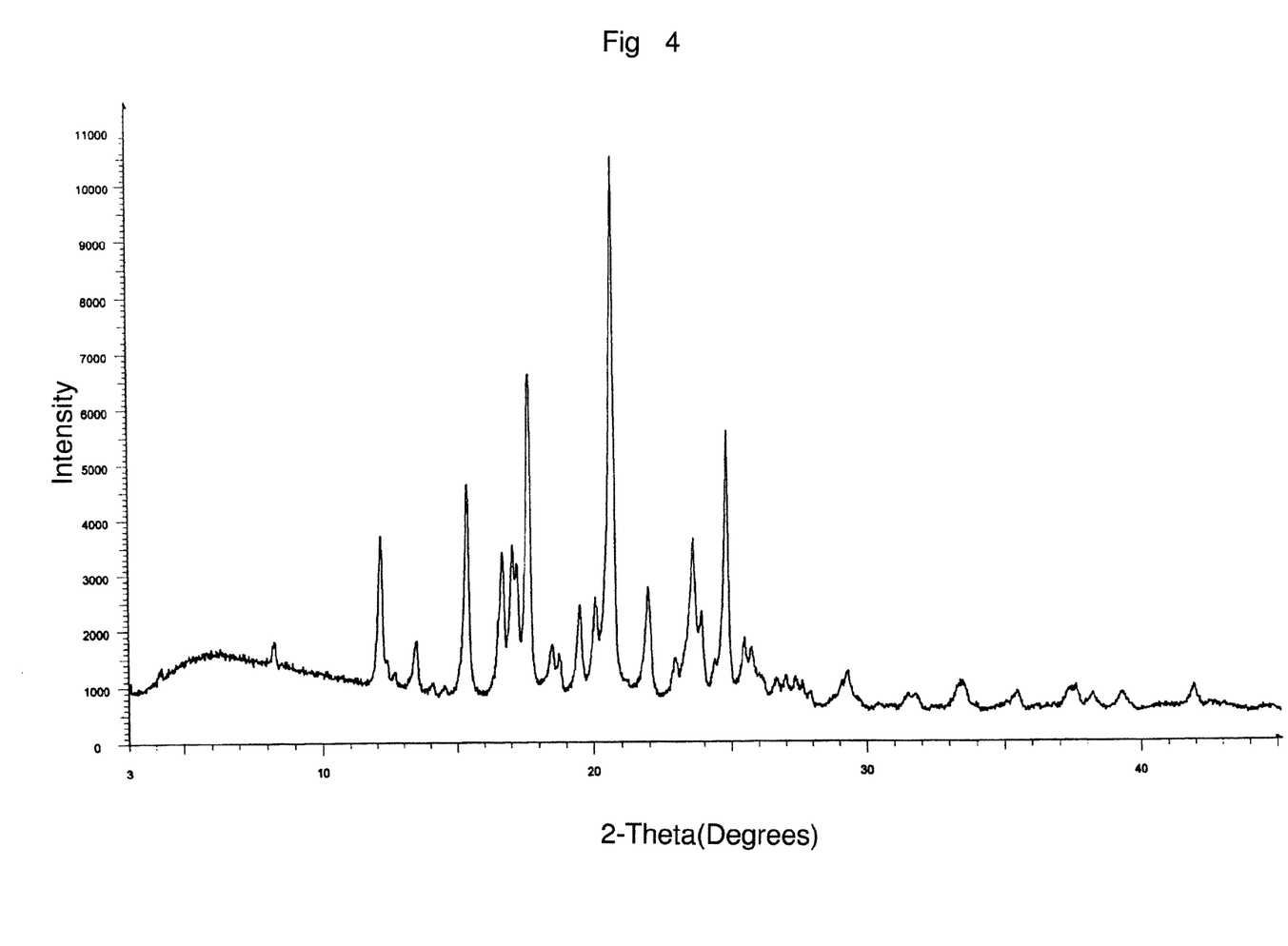
FIG. 4 is an XRPD pattern of an intimate mixture of aprepitant polymorphic Forms I and II in a ratio of about 95:5 w/w, prepared according to Example 4.
Figure 5:
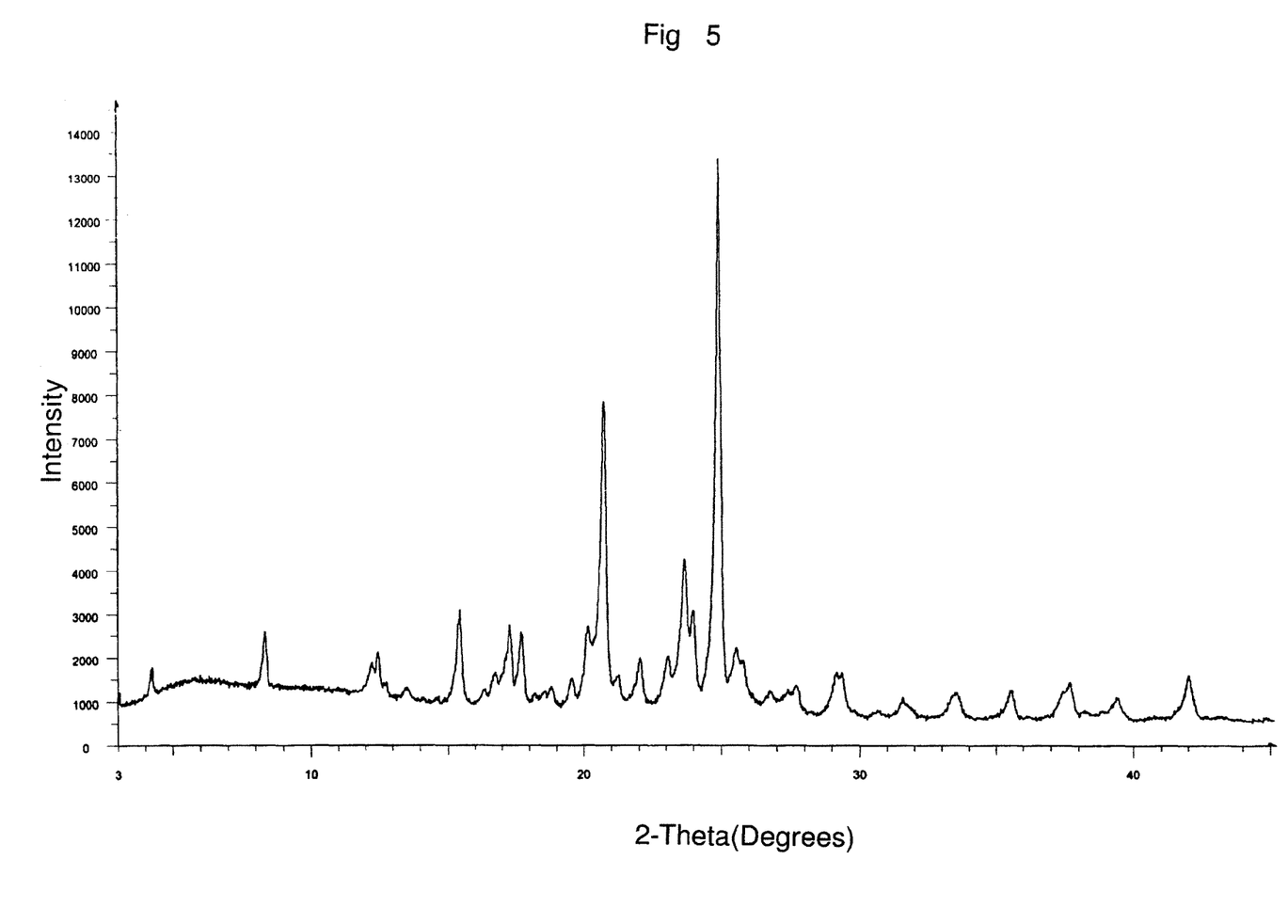
FIG. 5 is an XRPD pattern of an intimate mixture of aprepitant polymorphic Forms I and II in a ratio of about 75:25 w/w, prepared according to Example 5.
Figure 6:
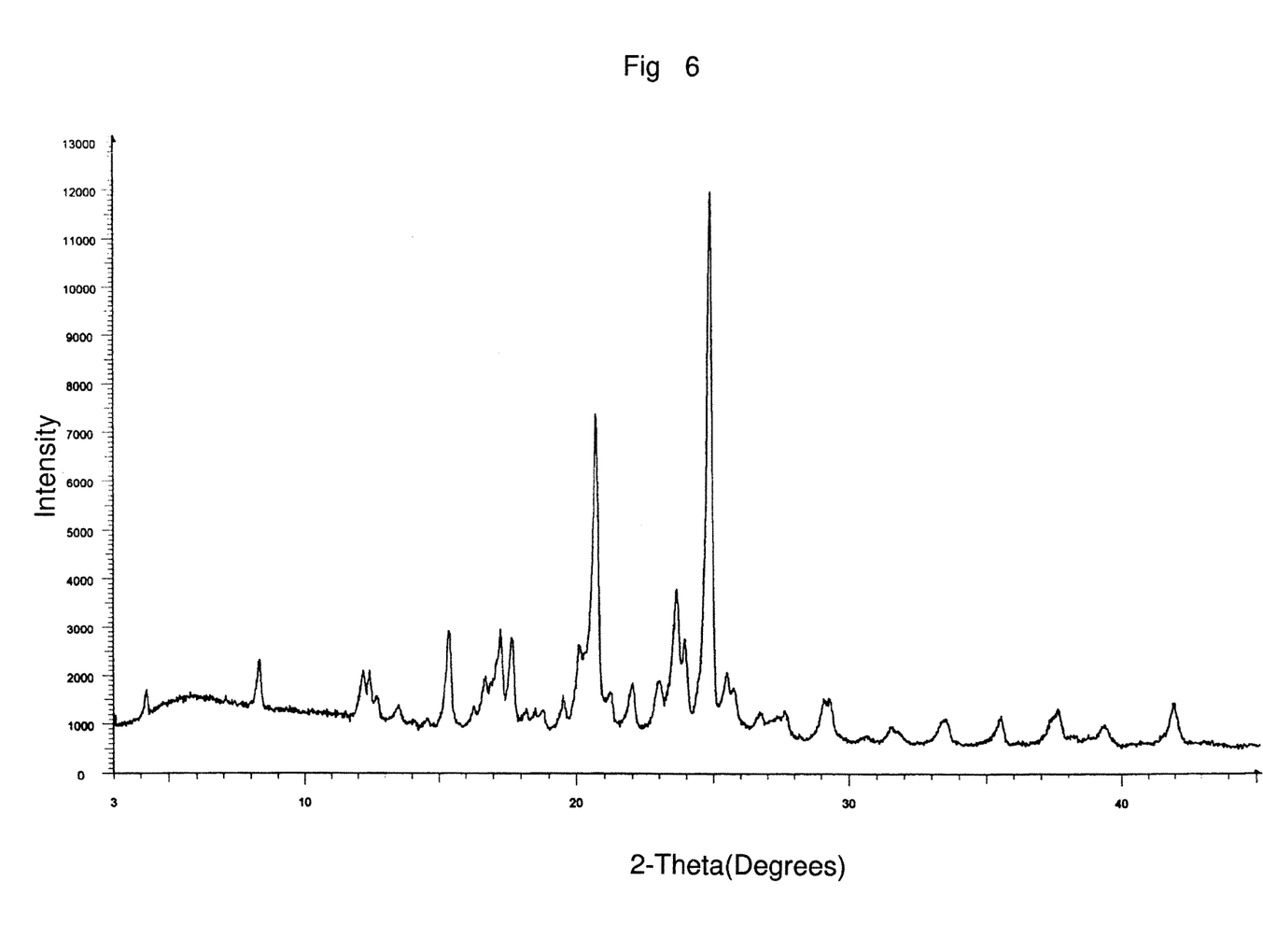
FIG. 6 is an XRPD pattern of an intimate mixture of aprepitant polymorphic Forms I and II in a ratio of 60:40 w/w, prepared according to Example 6.
Figure 7:
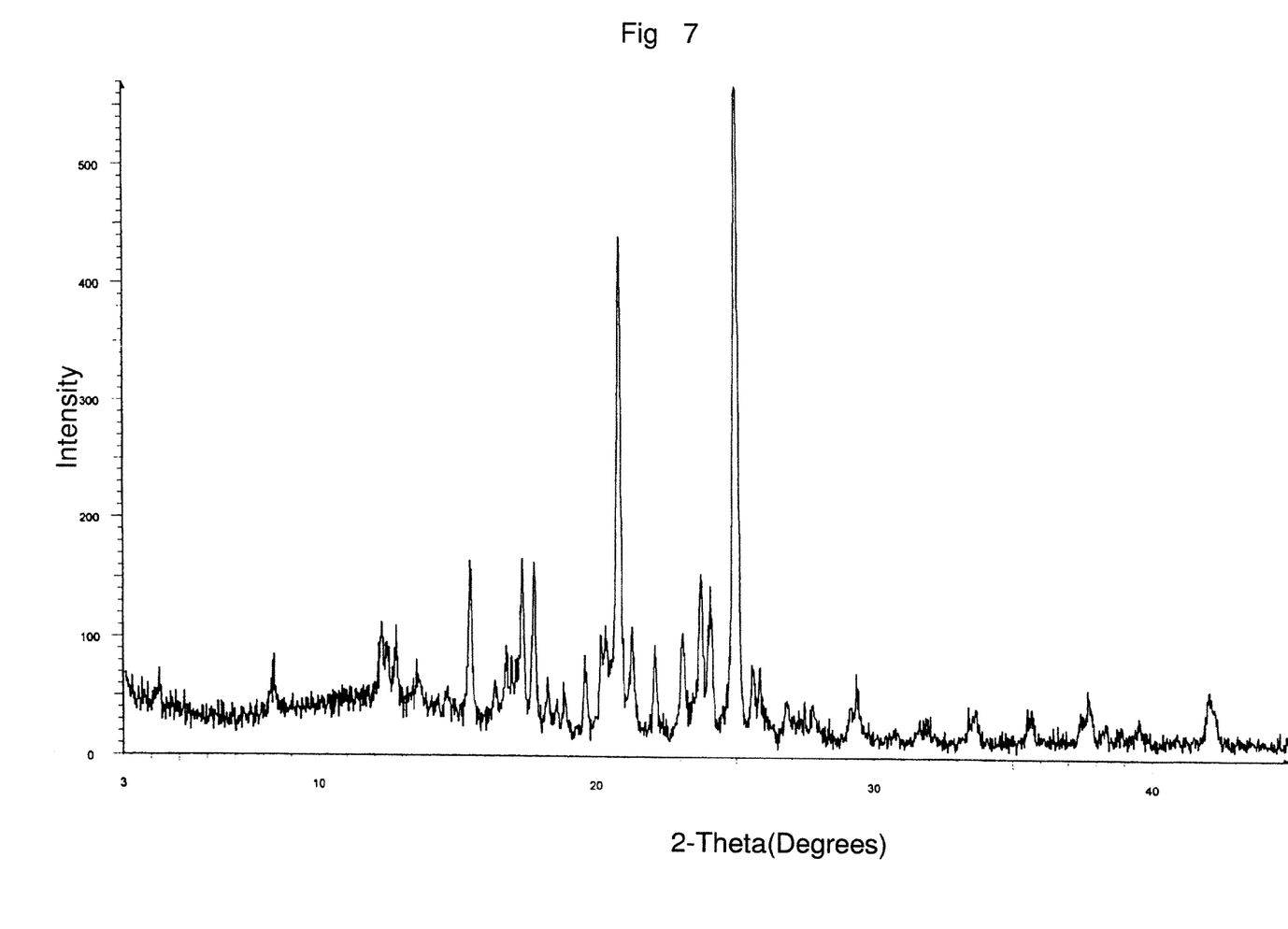
FIG. 7 is an XRPD pattern of an intimate mixture of aprepitant polymorphic Forms I and II in a ratio of about 50:50, prepared according to Example 7.
Figure 8:
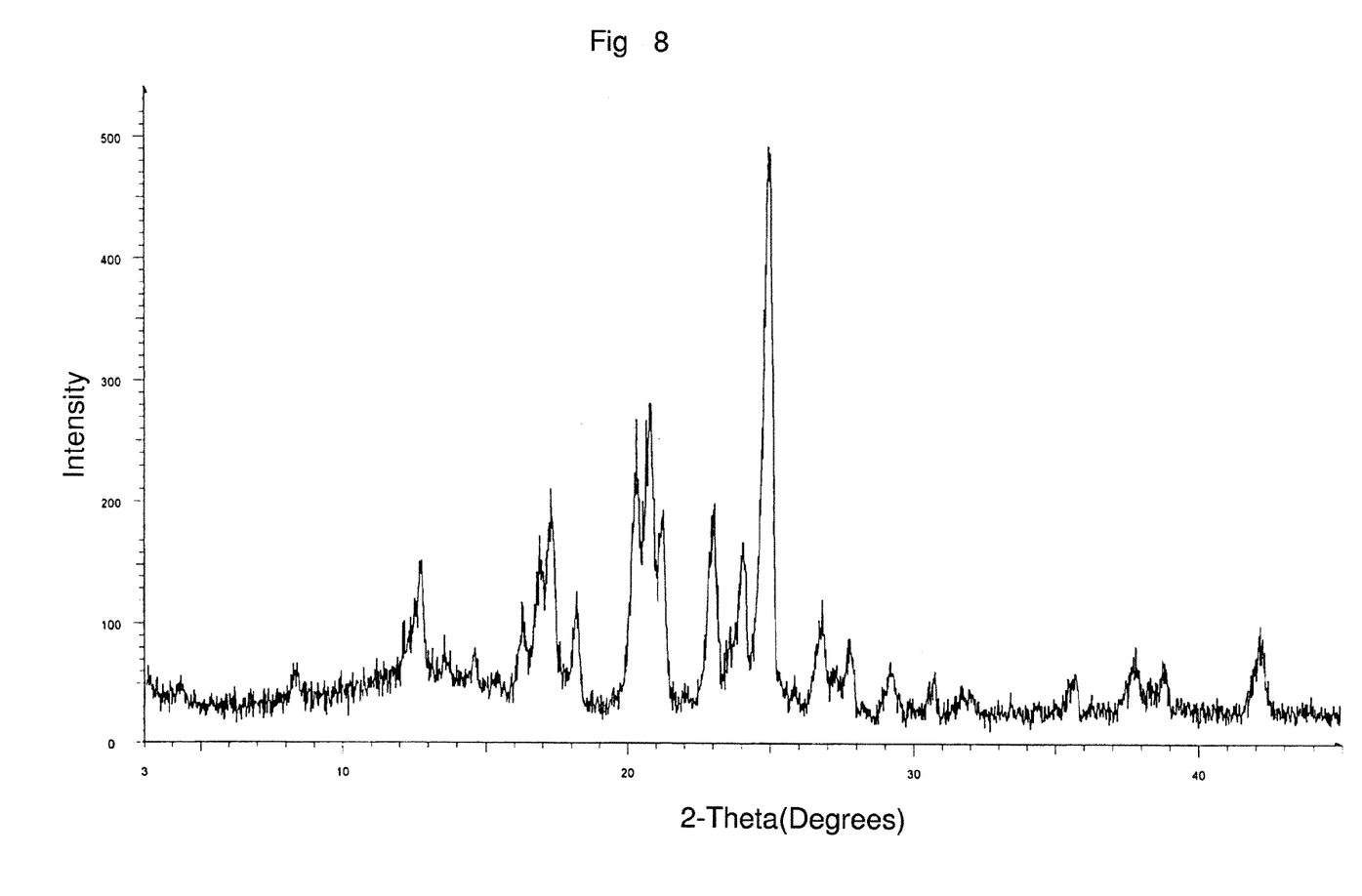
FIG. 8 is an XRPD pattern of an intimate mixture of aprepitant polymorphic Forms I and II in a ratio of about 25:75 w/w, prepared according to Example 9.
Figure 9:
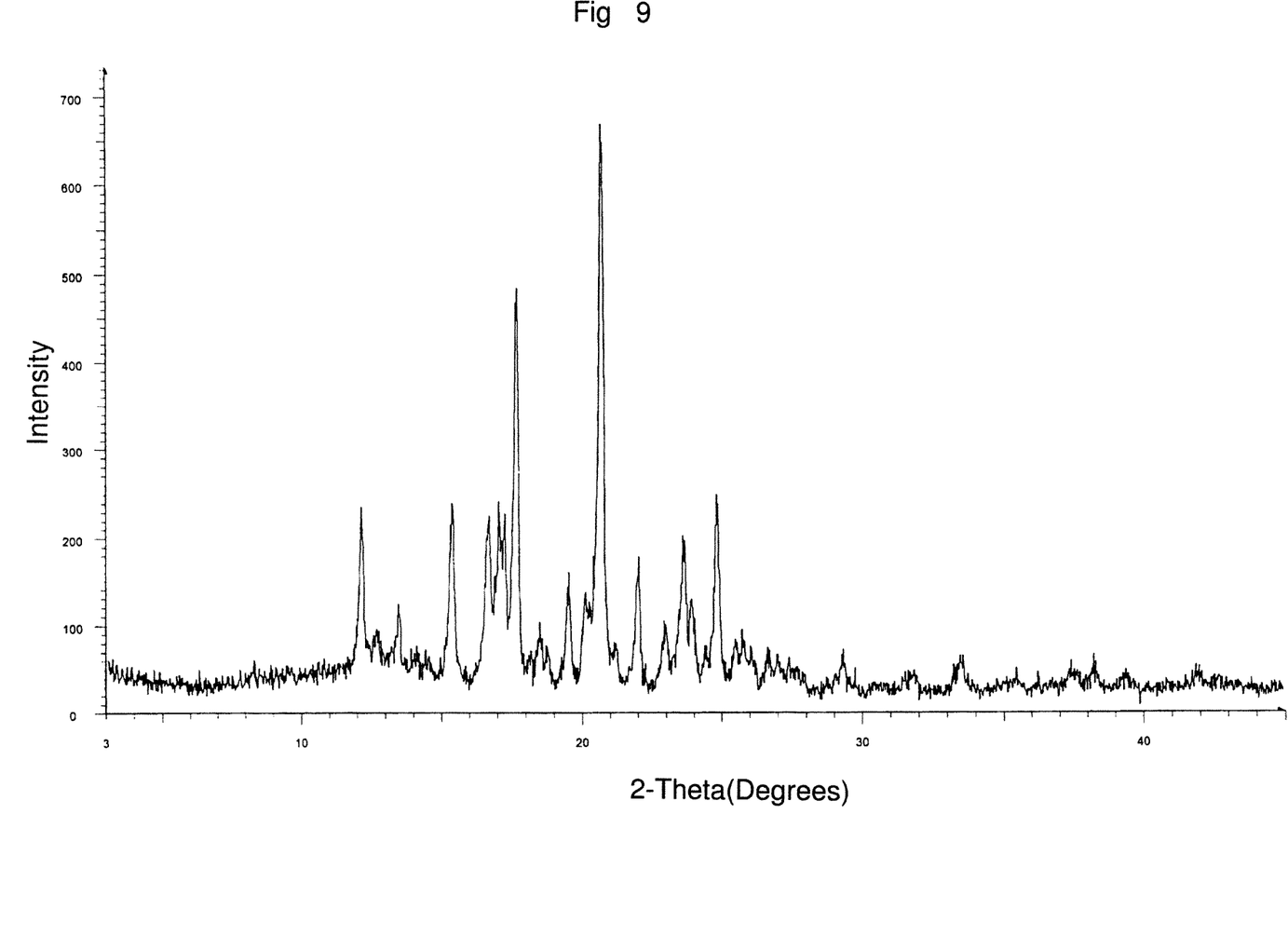
FIG. 9 is an XRPD pattern of an intimate mixture of aprepitant polymorphic Forms I and II in a ratio of about 80:20 w/w, prepared according to Example 11.
Figure 10:
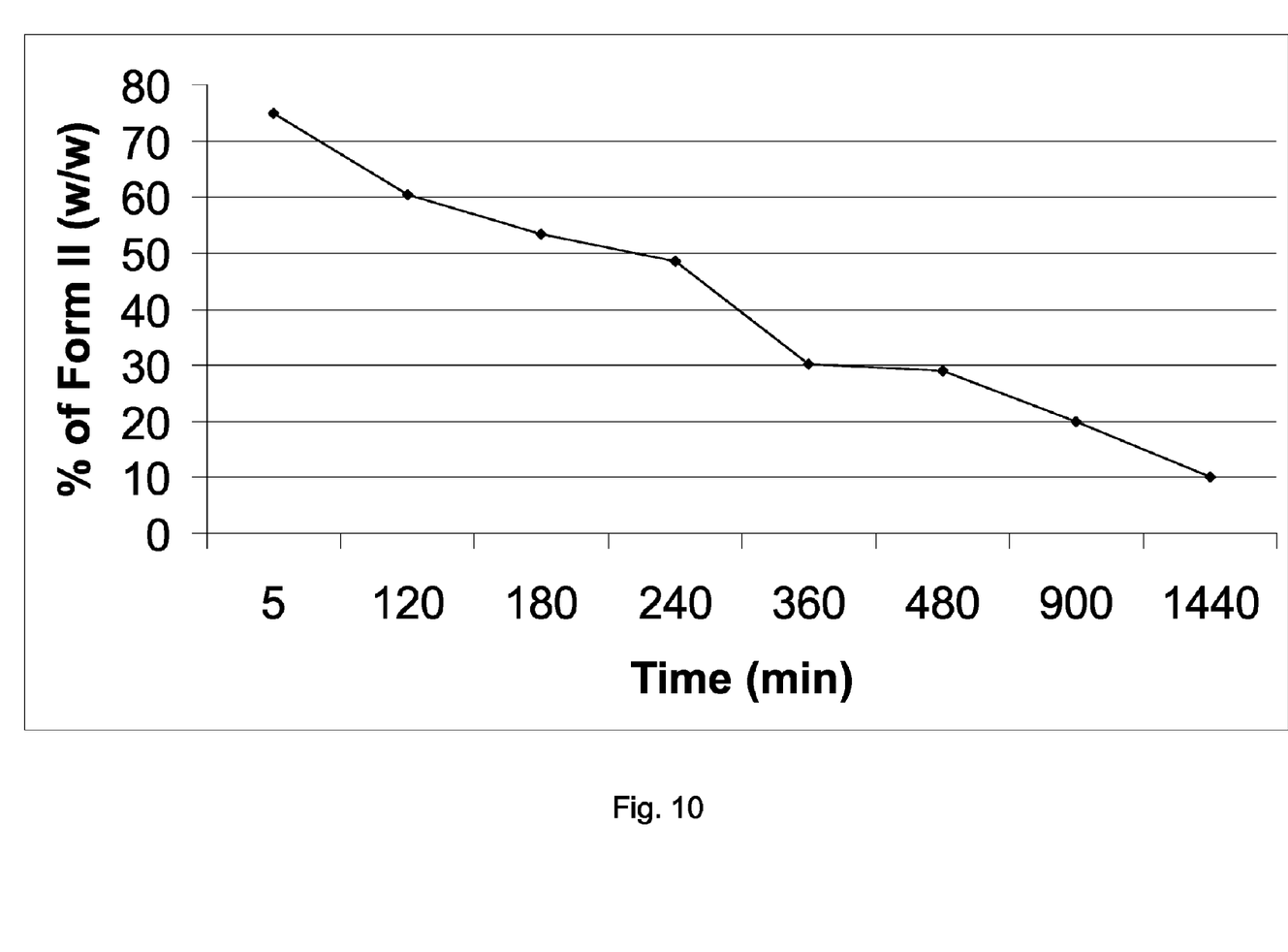
FIG. 10 is a graph showing variations in the percentage of Form II during maintenance of a formed solid in Example 16.

During the maintenance period, the ratio of crystalline forms is periodically determined and the results are plotted in the graph of FIG. 10.

From Examples 14, 15, and 16, it is evident that the percentage of Form II decreases with increasing maintenance time of the mixture, after solid formation. Hence, by adjusting the maintenance time, different desired ratios of aprepitant Form I to Form II can be obtained, as shown by the graph of FIG. 10.

Example 17

Preparation of a 50:50 Ratio of a Combination of Aprepitant Polymorphs I and II Using a Distillation Process 5 g of aprepitant, 250 ml of dichloromethane, 5 ml of methanol and 0.5 ml of 50% aqueous ammonia are charged into a clean and dry round bottom flask followed by stirring for 15 minutes. The solution is distilled completely at about 50° C. in a 4 neck round bottom flask at atmospheric pressure. The wet solid obtained is dried at 45° C. for 10 hours to afford 5 g of the desired intimate mixture of aprepitant polymorphic Form I to II in a weight to weight ratio of about 50:50.

Example 18

Determination of Aprepitant Form II in Form I by X-Ray Diffraction

Experimental conditions for performing the XRPD analysis for quantification were as follows:

| | |
|---|---|
| Instrument used | Powder X-ray diffractometer |
| Make, Model | Bruker AXS, D8 Advance |
| Goniometer | Theta/Theta vertical |
| Measuring circle | 435 mm |
| Radiation | Cu K α-1 (λ = 1.5406 A°) |
| Tube | 2.2 kW Copper long fine focus |
| Detector | PSD-VANTEC-1. |
| Voltage (kV), Current (mA) | 35 kV, 45 mA |
| Scan type | Locked coupled |
| Scan mode | Continuous scan |
| Divergence slit | 0.1 |
| Antiscattering slit | 0.5 deg. |
| Detector slit | 0.2 mm |
| Synchronuous rotation | On |
| Scan range 1 | 20.5° to 21.7° 2θ and ref peak range. |
| Scan range 2 | 14.5° to 15.7° 2θ |
| Step Size | 0.0082° |
| Time/Step | 1.5 sec. and 30.0 sec for ref peak. |
| Calculation | |

Process the diffraction peak for Form II≈21.15° (2θ) with constant smooth factor of 0.07 to check the detection of Form II and for the quantification of Form II the area of Form II peak and reference peak of Form I were taken.

The Form I and Form II areas of two preparations of the test sample were noted. Then average the Form I and Form II areas.

The percentage of Form II in Form I is calculated by the following formula:

% of Form $II=[(S2/S1)\div K=(S2/S1)]\times 100$

S1=Area of peak corresponding to Form I
S2=Area of peak corresponding to Form II
K=Response constant for Form II relative to Form I. The areas of the peaks associated with Form I and Form II (characteristic peaks) were measured using Bruker X-ray diffraction evaluation software. From these areas, the response constant for Form II relative to Form I was determined. The value for the K factor was 0.32.

The quantification limits of aprepitant Form II in Form I are between 5 and 95 percent by weight.

Example 19

Stability Studies for a Mixture of Aprepitant Form I and Form II In a Ratio of 50:50

A 50:50 weight ratio intimate mixture of aprepitant Form I and Form II prepared using the process of Example 12 was subjected to different conditions to determine the stability of the mixture under stress conditions. The results are tabulated below:

| Stress Condition | Form I to Form II Ratio After Stress |
|---|---|
| Grinding with a mortar and pestle at 25° C. for 30 minutes. | 45.5:54.5 |
| Micronization in an air-jet mill at a milling pressure of 3.0 kg/cm². | 48:52 |
| Micronization in an air-jet mill at a milling pressure of 6.0 kg/cm². | 46.8:53.2 |
| Drying in a fluid bed dryer at 90° C. for 4 hours. | 49:51 |
| Drying in a fluid bed dryer at 90° C. for 8 hours. | 50:50 |
| Drying in a Buchi Rotavapor under a vacuum of 700 mmHg at 90° C. for 24 hours. | 49.5:50.5 |
| Drying in a vacuum oven under a vacuum of 700 mmHg at 90° C. for 24 hours. | 50:50 |
| Drying in an air oven at 90° C. for 24 hours. | 51:49 |

Example 20

Powder Compositions of Aprepitant Mixture of Forms with Cyclodextrins (1:1 Molar Ratio)

2.12 g of β-cyclodextrin is dissolved in 100 ml of 2:3 by volume ratio of water to methanol and 1 gram of aprepitant mixture of forms (1:1 by weight) is added and dissolved. The solution is shaken for 6 hours at 50° C. The resultant solid is separated by filtration and dried in a tray drier at a temperature 50° C., till the loss on drying is 7.6% when measured at 80° C. using an infrared moisture balance.

Example 21

Powder Compositions of Aprepitant Mixture of Forms with a Combination of a Cyclodextrin and Wetting Agent (1:1.5 Molar Ratio)

0.925 grams of β-cyclodextrin is dissolved in 50 ml of water, 0.02 grams of Poloxamer 407 (block copolymer of ethylene oxide and propylene oxide) is added and dissolved, 0.29 grams of aprepitant mixture of forms (1:1 by weight) is added to this solution and the mixture is kept on a shaking machine for 6 hours at room temperature. The solid phase is separated by filtration and dried in a tray drier at a temperature of 50° C.

Example 22

Powder Composition of Aprepitant Mixture of Forms Containing a Polymeric Wetting Agent 500 mg of gelatin is dissolved in water and 100 mg of Poloxamer 407 is added and dissolved, 1 gram of aprepitant mixture of forms (1:1 by weight) is granulated using the solution. Granules obtained are dried at 50° C.

Example 23

Capsule Composition of Aprepitant Mixture of Forms 80 g of aprepitant intimate mixture of Forms I and II (1:1 by weight) is sifted through a 40 mesh ASTM sieve and is mixed with a pre-sifted mixture of 80 g of sucrose, 120 g of microcrystalline cellulose and 10 g of sodium starch glycolate, then blended with 5 g of magnesium stearate and 5 g of talc. The blend is filled into hard gelatin capsules, such that each capsule contains 80 mg of aprepitant.

The invention claimed is:

1. A crystallized intimate mixture of aprepitant crystalline Form I and crystalline Form II.

2. The intimate mixture of claim 1, wherein a weight ratio of Form I to Form II is about 5:95 to about 95:5.

3. The intimate mixture of claim 1, wherein a weight ratio of Form I to Form II is about 10:90 to about 90:10.

4. The intimate mixture of claim 1, wherein a weight ratio of Form I to Form II is about 25:75 to about 75:25.

5. The intimate mixture of claim 1, wherein a weight ratio of Form I to Form II is about 5:95.

6. The intimate mixture of claim 1, wherein a weight ratio of Form I to Form II is about 20:80.

7. The intimate mixture of claim 1, wherein a weight ratio of Form I to Form II is about 70:30.

8. The intimate mixture of claim 1, wherein a weight ratio of Form I to Form II is about 95:5.

9. The intimate mixture of claim 1, wherein a weight ratio of Form I to Form II is about 75:25.

10. The intimate mixture of claim 1, wherein a weight ratio of Form I to Form II is about 60:40.

11. The intimate mixture of claim 1, wherein a weight ratio of Form I to Form II is about 50:50.

12. The intimate mixture of claim 1, wherein a weight ratio of Form I to Form II is about 25:75.

13. The intimate mixture of claim 1, wherein a weight ratio of Form I to Form II is about 80:20.

14. A process for preparing a crystallized intimate mixture of aprepitant crystalline Form I and crystalline Form II, comprising:
    a) providing a solution comprising aprepitant and a suitable solvent;
    b) removing solvent from the solution; and
    c) optionally, drying a formed solid.

15. A process for preparing a crystallized intimate mixture of aprepitant crystalline Form I and crystalline Form II, comprising:
    a) providing a solution comprising aprepitant and a suitable solvent;
    b) combining an anti-solvent with the solution; and
    c) optionally, drying a solid formed in b).

16. The process of claim 15, wherein a solvent comprises acetone.

17. The process of claim 15, wherein an anti-solvent comprises water.

18. The process of claim 15, further comprising in b) adding seed crystals of an intimate mixture of aprepitant crystalline Form I and crystalline Form II in a desired product ratio, before, during, or after combining with an anti-solvent.

19. The process of claim 15, further comprising maintaining a combination of a solution and an anti-solvent until a mixture having a desired ratio of forms is obtained, then isolating a solid.

20. The process of claim 19, wherein maintaining is conducted at temperatures lower than the temperature of anti-solvent addition.

21. A process for preparing a crystallized intimate mixture of aprepitant crystalline Form I and crystalline Form II, comprising:
    a) providing a solution comprising aprepitant and acetone;
    b) combining water with a solution;
    c) maintaining a combination at temperatures lower than a temperature of combining, for a time sufficient to form a solid having a desired ratio of crystalline forms; and
    d) optionally, drying a formed solid.

22. The process of claim 21, wherein maintaining is at temperatures below about 5° C.

23. The process of claim 21, wherein a desired ratio of forms is a weight ratio of Form I to Form II about 5:95 to about 95:5.

24. The process of claim 21, wherein a desired ratio of forms is a weight ratio of Form I to Form II about 10:90 to about 90:10.

25. The process of claim 21, wherein a desired ratio of forms is a weight ratio of Form I to Form II about 25:75 to about 75:25.

* * * * *